United States Patent [19]

Grunwell et al.

[11] 4,073,899

[45] Feb. 14, 1978

[54] METHOD OF TERMINATING PREGNANCY

[75] Inventors: Joyce F. Grunwell, Hamilton; John O. Johnston, Cincinnati, both of Ohio

[73] Assignee: Richardson-Merrell, Inc., Wilton, Conn.

[21] Appl. No.: 661,967

[22] Filed: Feb. 27, 1976

Related U.S. Application Data

[62] Division of Ser. No. 506,255, Sept. 16, 1974, abandoned.

[51] Int. Cl.² .................. A61K 31/565; C07J 1/00

[52] U.S. Cl. .................. 424/238; 260/397.5; 260/397.4

[58] Field of Search .............. 260/397.5; 424/238

[56] References Cited

U.S. PATENT DOCUMENTS

| 3,413,287 | 11/1968 | Counsell et al. .............. 260/239.55 |
| 3,928,398 | 12/1975 | Grunwell et al. .............. 260/397.5 |

*Primary Examiner*—Elbert L. Roberts
*Attorney, Agent, or Firm*—William J. Stein; Eugene O. Retter; George W. Rauchfuss, Jr.

[57] ABSTRACT

7α-methyl-estr-5-ene-3β,17β-diol and 17-acyl esters as contragestative agents.

9 Claims, No Drawings

METHOD OF TERMINATING PREGNANCY

This is a division of application Ser. No. 506,255 filed Sept. 16, 1974, now abandoned.

SUMMARY OF THE INVENTION

This invention relates to a class of 7α-methyl-estr-5-ene-3β,17β-diols which are useful in terminating the pregnancy of higher female primates having defined menstrual cycles. More particularly this invention relates to compounds useful as contragestative agents for the termination of pregnancy and still more particularly as anti-implantation agents having the formula

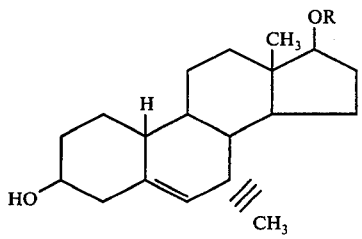

wherein R is selected from the group consisting of hydrogen and acyl having from 1 to 12 carbon atoms.

Additionally, an improved process for the preparation of 7α-methyl-estr-5-ene-3β,17β-diol is described.

BACKGROUND OF THE INVENTION

The use of pharmaceutical agents for the prevention and suppression of fertility in warm-blooded female mammals is well-known to the medical arts. At present, the most widely accepted of these pharmaceutical agents comprise mixtures of steroidal estrogens and progestins. The administration of these agents establishes a type of pseudopregnancy thereby preventing normal ovulation from occurring in the female. Although quite effective these agents are not without noticeable side effects. The most common side effects are similar to those symptoms observed during pregnancy and include nausea, gastric disturbances, headache, dizziness, fluid retention, breast discomfort and vascular disorders.

Various other types of contraceptive agents are also known to the art. Estrogens such as diethylstilbesterol and ethinyl estradiol have been used as postcoital contraceptive agents in the so-called "morning after pill." Such agenst are known to interfere with the tubal transport mechanism of the fertilized ovum, resulting in a preliminary expulsion of the fertilized ovum or blastocyst from the Fallopian tubes.

Contraception has also been achieved by disturbing the luteal phase of the uterine lining. A suitably prepared endometrium is necessary for successful implantation or nidation of the blastocyst. Such agents act in a manner which interferes with the formation of the luteal or secretory phase of the uterine lining. Alternatively, such agents may delay or retard the formation of the luteal phase of the uterine endometrium thereby resulting in a desynchronization of uterine development with respect to blastocyst implantation.

Various intrauterine devices have also been employed for the prevention of pregnancy. Such devices require medical insertion and are not a totally effective means for the prevention of pregnancy. Occasionally, devices of this type are involuntarily expelled and will also cause intrauterine irritation and/or bleeding.

Thus, there is a need for both new and better pharmaceutical agents useful in the prevention of pregnancy as well as new and better methods for the administration of existing antifertility agents. In particular there is a need for a highly effective therapeutic measure which can be self-administered and which requires a minimum of drug exposure.

As a result of a long series of investigations, applicants have made the important discovery that 7α-methyl-estr-5-ene-3β,17β-diol and its 17β-ester derivatives are highly effective contragestative agents useful in those higher primates which have a well-defined menstrual cycle. These compounds are useful in terminating pregnancies at a very early stage. Thus, whereas the estrogen-progestin mixtures now most widely used must be administered for relatively long periods in anticipation of coitus, and whereas postcoital contraceptive agents are administered less frequently but nevertheless administered on a regular basis, the compounds of the present invention are administered on a month to month basis, and then for only a relatively short period of time prior to or about the expected time of menses.

U.S. Pat. No. 3,380,886 represents the closest art known to applicants. Disclosed therein are 7α-methyl-3β-hydroxy-5-androstenes, in general, and the compound 7α-methyl-estr-5-ene-3β,17β-diol as having antifertility activity, namely in the inhibition of conception.

Applicants have discovered that the compound, 7α-methyl-estr-5-ene-3β,17β-diol and its 17-esters, when administered during the implantation stage are highly effective as contragestative agents in terminating an aready existing pregnancy. Thus, it is not necessary to administer these compounds on a day to day basis during most of the menstrual cycle in order to prevent pregnancy from occurring. In contradistinction thereto, it has been discovered that these compounds can be effectively administered subsequent to conception and during the early stages of gestation.

DETAILED DESCRIPTION OF INVENTION

Whereas the compound 7α-methyl-estr-5-ene-3β,17β-diol represents the compound of choice for use in the instant invention, those 17β-acyl esters, having from 1 to 12 carbon atoms, are also within the scope of this invention as indicated in Formula I above.

The acyl esters are derived from mono-basic alkyl or aralkyl carboxylic acids having from 1 to 12 carbon atoms. The carboxylic acids from which these acylates are derived include both saturated and unsaturated aliphatic acids as well as aromatic acids. These acids include, for example, such acids as acetic, propionic, butyric, isobutyric, valeric, isovaleric, caproic, caprylic, decanoic, dodecanoic, acrylic, crotonic, cyclobutanecarboxylic, cyclopentanecarboxylic, cyclopentenecarboxylic, cyclohexanecarboxylic, benzoic, toluic, naphthoic, ethylbenzoic, phenylacetic, naphthaleneacetic, phenylvaleric, cinnamic, phenylpropionic, p-propyloxylphenylpropionic and p-butyloxylphenylacetic acid. Preferably, the lower aliphatic acids containing from 1 to 6 carbon atoms are employed, and even more particularly, the acetyl ester is employed.

U.S. Pat. No. 3,380,886 describes the preparation of 7α-methyl-estr-5-ene-3β,17β-diol starting with the compound 19-nor-4,6-androstadiene-3,17-dione. Initially, this compound is treated with methylmagnesium bromide in the presence of cuprous chloride to introduce the 7-methyl substituent. The reaction mixture is treated with acetic anhydride to obtain the Δ$^{3,5}$-enolester. Introduction of the methyl group results in the preparation of both 7α and 7β-isomers. Purification of the crude material is by a fractional crystallization, chromatography or other conventional means of separation with concomitant low yields. The enolester is then treated with sodium borohydride to obtain the desired 7α-methyl-estr-5-ene-3β,17β-diol in poor yield.

As an improvement thereover, the preparation of 7α-methyl-estr-5-ene-3β,17β-diol in accordance with the present invention is greatly facilitated and achieved in a fewer number of steps and a greater yield by the reduction of 7α-methyl-estr-5-en-3-ones by means of complex aluminum hydrides such as lithium aluminum hydride and lithium tritertiarybutoxyaluminum hydride. The 7α-methyl-estr-5-en-3-ones are prepared by alkylating the corresponding 17β-hydroxy-4,6-estradien-3-one, 17β-hydroxy-4,6-estradien-3-one acetate, or 4,6-estradiene-3,17-dione with dimethyllithium copper in an inert solvent, such as diethyl ether, tetrahydrofuran, hexane or mixtures thereof at temperatures ranging from -78° to 25° C. Quenching the initially formed enolate anion with a weak protonating agent such as a saturated solution of ammonium chloride, oxalic acid or boric acid provides the 7α-methyl-estr-5-en-3-ones.

The intermediates so obtained, namely 17β-hydroxy-7α-methyl-estr-5-en-3-one, 17β-hydroxy-7α-methyl-estr-5-en-3-one acetate and 7α-methyl-estr-5-ene-3,17-dione are reduced at the 3-position to the equatorial beta alcohol by the action of complex aluminum hydrides such as lithium aluminum hydride or lithium tri-tertiarybutoxyaluminum-hydride. The reduction is performed in solution in an inert organic solvent, such as diethyl ether, glycol dimethylether or tetrahydrofuran, the latter being the solvent of choice. Reduction temperatures can vary from -78° C. to the reflux temperature of the solvent with temperatures ranging from 0° to 25° C. being preferred.

In general a solution of the 7α-methyl-estr-5-en-3-one in an ether such as tetrahydrofuran is purged with nitrogen. This solution is slowly added to a solution of a complex aluminum hydride, which has also been purged with nitrogen. The reaction mixture is stirred at room temperature for a period ranging from 4 to 36 hours and excess hydride is destroyed by cautiously adding water or an aqueous solution of sodium potassium tartrate. The solid which forms is removed by filtration and the filtrate dried and concentrated. Alternatively the aqueous mixture can be extracted with an organic solvent such as methylene chloride or ethyl acetate. The organic extract is washed with water, dried and concentrated. The residue containing the 7α-methyl-estr-5-ene-3β,17β-diol is further purified by conventional means. When lithium aluminum hydride is used for the reduction, any ester present at the 17-position will be hydrolyzed to the free alcohol. Conversely when lithium tri-tertiary-butoxyaluminum hydride is employed, an ester at the 17-position remains intact. Both reagents, however, will reduce a 17-ketone to a 17β-alcohol.

The term higher primates as used herein includes those species of primates in which the female usually has a more or less regualr menstrual cycle. Such species include the rhesus monkey, orangutan, chimpanzee, baboon, gorilla and the human.

For the purposes of this application a pregnancy is a condition of female primates wherein a fertilized ovum is contained in their reproductive tract. In addition for purposes of this invention, the gestation period is presumed to begin at the point of fertilization.

The term nidation period as used herein refers to that period of time during which the fertilized ovum or blastocyst attaches itself and penetrates the epithelial uterine lining.

The term implantation period refers to that period of time during which the fertilized ovum or blastocyst begins the formation of a placental membrane and establishes an interconnection with the maternal blood supply. While the exact mechanism or mechanisms which take place with the active ingredients of this invention in terminating a pregnancy are not clear, it is known that the compositions of this invention interfere in some manner with the implantation process and the maternal ability to support the embryo or fetus, thereby interrupting the gestation period at a very early stage. Since abortifacient agents are generally associated with a later stage of development in pregnancy, the compounds of this invention as used herein may more properly be called anti-implantation agents or contragestative agents and not abortifacients.

The female rhesus monkey and the female baboon are useful primate models for the study of anti-implantation and contragestative agents due to the close similarity of their menstrual cycles with that of the human female. However, the size and temperament of these animals, plus the expense of maintaining large primate colonies, make these animals unsuitable for the routine screening and testing of compounds. Whereas in the rat the implantation process and the maintenance of pregnancy is dominated by the presence of estrogen, in the hamster as with higher primates the implantation process and maintenance of pregnancy is dominated by the presence of progesterone. Accordingly, a high degree of correlation exists between the hamster and higher primates. The pregnant hamster is a more practicable and manageable animal model that can be accommodated in the large numbers required for the successful testing of compounds. The pregnant hamster is therefore a standard experimental animal model employed for the evaluation of anti-implantation agents by those skilled in the art.

The effect of these compounds on implantation is demonstrated by their administration to pregnant hamsters at a point subsequent to nidation and observing their prepartum effects. Mated female hamsters, considered to be pregnant as a result of the presence of sperm in a post-estrus vaginal lavage, are administered the test compound subcutaneously during days 8-12 of pregnancy. This period of gestation in the hamster relates from a point just subsequent to nidation of a fertilized ovum or blastocyst to a point after which implantation has occurred and placental circulation is now complete. Treated animals are terminated 1 day prior to parturition and the total number of live feti is compared to those in a control group of mated female hamsters.

In addition to the anti-implantation or contragestative effects, the compound 7α-methyl-estr-5-ene-3β-17β-diol and its 17-acyl esters demonstrate antiprogestational activity with concomitant low estrogenicity and are useful for reducing fertility in such commercially valuable species as dogs, cats, cows and horses.

The active compounds of this invention may be conviently administered either bucally, intrauterinly or intravaginally. The particular dosage employed depends, of course, upon such factors as the specific route of administration, the frequency of dosing, and the weight and age of the particular higher primate being dosed. In general the amount of a single daily dose required to produce the desired level of efficacy is such as to provide a proportionate dosage of from 0.1 mg. to 500 mg. of active ingredient. Suitable dosage forms may be administered one or more times a day or for more than 1 day during the period of administration.

The compounds of this invention can be administered during the period of implantation which immediately follows the period of nidation. In higher female primates having a 26–32 day menstrual cycle, the nidation period corresponds approximately to days 18–23 of the menstrual cycle, having the onset of the last menstruation counted as day one of the menstrual cycle. The period of implantation generally begins on or about day 21 of the same cycle and within 14 days placental circulation is generally considered to be complete.

In human females nidation generally occurs on or about the 20th day of the menstrual cycle. Implantation generally occurs on or about day 21 of the same cycle and by about day 35 placental circulation is considered to be complete. Thus, the compounds of the present invention are administered on or about 21 days after the onset of menstrual bleeding. Administration can be continued for a period of from 1 to b 14 days or until menstruation again commences indicating that pregnancy, if any, has been terminated. In the event that a single dose is to be administered, this may most advantageously be administered on day 21 or day 22 of the cycle.

A convenient mode of administration is to administer the compounds of this invention on or about the expected times of menses. The expression "on or about" the expected time of menses is utilized to accommodate normal variations in menstrual cycles. For purposes of this invention the terms includes up to 3 days prior or subsequent to the normal menstrual cycle. Thus, in human females the compositions of this invention can be conveniently administered on days 25 to 31 of the menstrual cycle. Obviously, if menstrual bleeding occurs, indicating a lack of pregnancy, further administration of medicament is unnecessary.

The compounds of the present invention are administered in various dosage unit forms. They may be taken bucally in the form of lozenges or troches containing an inert diluent or assimilable edible carrier. Another form of administration is via the intravaginal route. This route of administration provides local administration of medicament where it can be directly absorbed by the vaginal and cervical mucosa. Useful preparations for this purpose include vaginal creams, jellies ad ointments. Topical ointments of the active ingredient in a suitable ointment base such as petrolatum, lanolin, polyethylene glycols or mixtures thereof are useful for such administration. Generally the steroid is finely divided by milling or grinding. Creams and lotions are also suitable and are prepared by dispensing the active ingredient in an oily phase and subsequently forming an emulsion therefrom. A preferred formulation for vaginal administration is a stable, non-aqueous, aerosol foam which readily collapses at body temperatures and spreads as a uniform film along the walls of the vagina. These compositions are cosmetically superior in that they do not produce a sensation of warmth or dehydration when applied due to the inhibition of normal moisture evaporation. Additionally, they are not greasy or tacky and will not stain underclothing. Soft cushiony foams can be prepared which after introduction into the vagina and warming to body temperature will flatten and leave a thin film of medicament evenly distributed along the vaginal walls.

Another form of administration particularly convenient and useful is a medicated tampon containing the active ingredient. Such a tampon applied on or about the expected arrival of menses, releases the active ingredient at a suitable, predetermined rate. In the event that a pregnancy has occurred the release of the active ingredient and its subsequent local absorption serves to terminate the pregnancy and thereby restore normal menses.

The following examples illustrate the novel process for the preparation of 7α-methyl-estr-5-ene-3β,17β-diol, the anti-implantation and contragestative effect of this compound and its acyl esters in pregnant hamsters and various formulations for oral, uterine or vaginal administration.

EXAMPLE 1

3,17β-Diacetoxyestr-3,5-diene

The compound, 19-nortestosterone, 400 g., is refluxed under nitrogen in a mixture of 1500 ml. of acetic anhydride and 1500 ml. of acetyl chloride for a period of about 3 hours. The volatile solvents are distilled at atmospheric pressure and the final traces of solvent removed under reduced pressure. The solid residue which remains is triturated with ice water, filtered, washed with a cold aqueous sodium bicarbonate solution, rinsed with water and dried. Two recrystallizations of this residue from acetone yields 370 g. of 3,17β-diacetoxyestr-3,5-diene which melts at 165°–71° C.

EXAMPLE 2

17β-Hydroxyestra-4,6-dien-3-one acetate

The compound, 3,17β-diacetoxyestr-3,5-diene, 60.0 g. (0.158 mole) prepared as in Example 1, is placed in an acetone-buffered solution comprising 3,180 ml. of acetone, 816 ml. of water, 81,6 ml. of acetic acid, 18 ml. of pyridine and 81,6 g. of sodium acetate. The solution is cooled to 0°–5° C. using a salt-methanol-ice bath and 32.1 g (0.18 mole) of N-bromosuccinimide is added at one time.

The reaction mixture is totally shielded from light and stirring continued for a period of about 3 hours at 0°–5° C. The solution is poured onto 12 liters of cold brine and the product extracted with 1 liter of ether. The ether extract is separately washed with water, dried over anhydrous magnesium sulfate and concentrated under vacuum at temperatures below 20° C. The amber oil which remains as a residue is dissolved in 75 ml. of dimethylformamide and this solution is rapidly added to a vigorously refluxing suspenson of 750 ml. of dimethyformamide, 60 g. of lithium bromide, and 60 g. of lithium carbonate under nitrogen.

Residual ether is permitted to evaporate and the reaction mixture is refluxed for a period of 1 hour. On cooling, the suspension is filtered and the filtrate is poured into an ice-water mixture. The product is extracted into ether ad the combined ether extracts are washed again with water. The solution is dried over anhydrous magnesium sulfate and concentrated under vacuum to yield a yellow solid which is layered with hexane and filtered to yield 34.6 g. of the desired 17β-hydroxyestra-4,6-dien-3-one acetate.

EXAMPLE 3

17β-Hydroxy-7α-methylestr-5-en-3-one acetate

A solution of lithium dimethylcopper is prepared under nitrogen by the addition of 1 mole of 1.6 M ethereal methyllithium to a slurry of 99 g. (0.52 mole) of cuprous iodide contained in 1000 ml. of anhydrous ether at 0° C. The solution is stirred at this temperature for 5 minutes and a solution of 35 g. (0.11 mole) of 17β-hydroxyestra-4,6-dien-3-one acetate, prepared as in Example 2, contained in 300 ml. of anhydrous tetrahydrofuran is added over a 10 minute period. The reaction mixture is stirred for an additional 15 minutes at 0° C. and poured into a saturated aqueous ammonium chloride solution. Benzene is added and the resulting mixture is rapidly filtered through a bed of diatomaceous earth. The organic layer is washed with a saturated aqueous ammonium chloride solution, washed with water, dried over anhydrous magnesium sulfate and evaporated to dryness. The crude product is layered with hexane and cooled overnight to yield 25 g. of 17β-hydroxy-7α-methylestr-5-en-3-one acetate.

EXAMPLE 4

7α-methyl-5-estrene-3β,17β-diol

A suspension of 9.5 g. (0.25 mole) of lithium aluminum hydride is added to 1000 cc. of diethylether under nitrogen. To this suspension is added 40.0 g. (0.12 mole) of 17β-hydroxy-7α-methyl-5-estren-3-one acetate contained in 500 ml. tetrahydrofuran over a 40 minute period. The reaction is stirred at room temperature overnight. To this reaction mixture is added 200 ml. of wet ether followed by the addition of water. The suspension is filtered, the filtrate dried over magnesuim sulfate and concentrated under vacuum. Two recrystallizations from acetone-hexane yields 27.5 g. of the desired 7α-methyl-5-estrene-3β,17β-diol, M.P. 204°-208° C.

Anal. Calcd. for $C_{19}H_{30}O_2$: C, 78.57; H, 10.41. Found: C, 78.67; 78.58; H, 10.39, 10.49.

Following essentially the same procedure but substituting 17β-hydroxy-7α-methyl-estr-5-en-3-one or 7α-methyl-estr-5-en-3,17-dione for the 17β-hydroxy-7α-methyl-estr-5-en-3-one acetate above, also results in the preparation of the desired 7α-methyl-estr-5-ene-3β,17β-diol.

EXAMPLE 5

7α-Methyl-estr-5-ene-3β,17β-diol acetate

A solution of 17β-hydroxy-7α-methyl-estr-5-en-3-one acetate dissolved in tetrahydrofuran is purged with nitrogen and slowly added to a suspension of lithium tertiarybutoxyaluminum hydride also purged with nitrogen. The mixture is stirred at room temperature for about 16 hours and excess hydride is destroyed by cautiously adding a solution of sodium potassium tartrate. The solid which forms is removed by filtration and the filtrate is extracted with methylene chloride. The combined methylene chloride extracts are washed with water, dried and concentrated under vacuum. Recrystalization of the residue from acetone-hexane yields the desired 7α-methyl-estr-5-ene-3β,17β-diol acetate.

EXAMPLE 6

Anti-implantation Activity

Commercially available female hamsters are mated and made pregnant by cohabitating with males overnight. Vaginal smears are taken on the following morning to see if they are sperm positive. The day of a positive smear is designated as day 1 of pregnancy. Test animals are placed in groups of eight with two to three animals per cage under cnditions which enable a control of temperature, humidity, air flow, feed and water. The test group of animals are treated on days 8, 9, 10, 11 and 12 of pregnancy with the test compound by subcutaneous administration. This period of treatment in the hamster roughly corresponds in the fertile human female from a point after nidation to a point subsequent to the ovarian-placental shift, i.e., the point at which placental circulation is complete. Treatment in vehicle only control groups are sacrificed on day 15 of pregnancy. At necropsy each animal is classified as pregnant with live feti, as not pregnant with resorbed uterine implantation sites, or as not pregnant with no evidence of conception having taken place. The antifertility activity is indicated by a decrease in the total number of live feti (TLF) in the treatment group as compared to those in the vehicle control group.

Using this test system, the compound 7α-methyl-estr-5-ene-3β,17β-diol when subcutaneously administered during days 8 through 12 of pregnancy demonstrates a high degree of anti-implantation activity as indicated in Table I.

Table I

| Compound | Dose mg/kg/day (s.c.) | No. Pregnant Animals Total Animals Treated* | TLF* |
|---|---|---|---|
| 7α-Methylestr-5-ene-3β,17β-diol | 30.0 | 0/8 | 0 |
|  | 10.0 | 3/8 | 4 |
|  | 3.0 | 2/8 | 6 |
|  | 1.0 | 8/8 | 91 |
| Vehicle Control | — | 8/10 | 84 |

*Sacrificed on day 15 of a 16-day gestation.

EXAMPLE 7

Antiprogestational Activity

The compound 7α-methylestr-5-ene-3β,17β-diol was tested in vivo for its antiprogestational activity under the following standardized laboratory conditions. Groups of 10 immature female rats were treated over a 10-day period at age 28-36 days. One group of 10 animals received a daily dosage of 40 mg./kg. of progesterone. A second group of 10 animals received 40 mg./kg. of progesterone and, in addition, concurrently received a dosage of from 0.001 to 3.0 mg./kg. of the test compound. A third group of 10 animals served as the vehicle control group. At day 5 of treatment, the right uterine horn of all animals was traumatized using a burred needle to simulate pseudo-implantation. The animals were sacrificed at day 37 of age and the uterine horns, both the traumatized horn and the untraumatized control uterine horn were separately weighed. The percent increase in mean uterine horn weight of the traumatized horn over the untraumatized is indicated in Column 3. The result is expressed in Column 4 as a percent inhibition of the progesterone control group.

Table II

| Compound | Number of Animals | Dose mg/kg (s.c.) | Increase in traumatized horn over the contralateral horn % | % Progesterone Control |
|---|---|---|---|---|
| 7α-Methylestra-5-ene-3β,17β- | 18 | 3.0 | 89.7 | 17.5* |
|  | 16 | 1.0 | 86.8 | 17.0* |

Table II-continued

| Compound | Number of Animals | Dose mg/kg (s.c.) | Increase in traumatized horn over the contralateral horn % | % Progesterone Control |
|---|---|---|---|---|
| diol | 20 | 0.1 | 82.0 | 16.0* |
|  | 20 | 0.03 | 157.8 | 30.7* |
|  | 20 | 0.01 | 270.6 | 52.8 |
|  | 10 | 0.003 | 700.2 | 136.6 |
|  | 10 | 0.001 | 659.3 | 128.6 |
| Progesterone Control | 36 | 40.0 | 512.7 | 100 |

*Statistical difference between drug-treated and progesterone-treated control (p ≦ 0.01).

EXAMPLE 8

Preparation of a Longlasting Troche

An illustrative preparation of 1500 troches, each weighing 750 mg. is formulated as follows:

| | Ingredients | Gms. |
|---|---|---|
| (a) | 7α-methyl-estr-5-ene-3β,17β-diol | 15.0 |
| (b) | Pectin | 370.0 |
| (c) | Gelatin | 370.0 |
| (d) | Sodium carboxymethylcellulose | 370.0 |

The diol is admixed with approximately 10 gm. of pectin. The remainder of the pectin and other ingredients are added and thoroughly mixed. The resulting mixture is compressed into capsule-shaped troches. Each troche so prepared contains 10 mg. of 7α-methyl-estr-5-ene-3β,17β-diol.

EXAMPLE 9

Preparation of a Hard Candy Lozenge

The following formulation can be utilized in the preparation of approximately 9,000 lozenges weighing 5.0 gm. each.

| | Ingredients | Weight | |
|---|---|---|---|
| (a) | 7α-methyl-estr-5-ene-3β,17β-diol | 90 | gms. |
| (b) | Sodium cyclamate | 450 | gms. |
| (c) | Saccharin Sodium | 45 | gms. |
| (d) | Cetyl diethyl benzylammonium chloride | 27 | gms. |
| (e) | Benzocaine | 45 | gms. |
| (f) | Granular Sugar | 28 | kgs. |
| (g) | Liquid Glucose (43°) | 16.7 | kgs. |
| (h) | Sour orange flavor q.s. Wild cherry flavor q.s. | | |

The granular sugar is placed into a pre-cook kettle together with 14 liters of water. The mixture is brought to a boil and the sodium cyclamate is added and dissolved with stirring. The glucose is added and the mixture brought to a predetermined temperature of 135° C.

The composition is transferred to a continuous vacuum cooker and reduced to a proper consistency for a candy base. The remaining ingredients are added to this candy base with stirring. The mixture is thoroughly kneaded and a continuous rope formed. Lozenges weighing approximately 5.0 gm. each and containing about 10.0 mg of 7α-methyl-estr-5-ene-3β,17β-diol are cut from the rope, packaged and distributed in any convenient manner.

EXAMPLE 10

Preparation of an Ointment Formulation

One thousand grams of an ointment for topical application contaning 1.0% of 7α-methyl-estr-5-ene-3β,17β-diol acetate are prepared as follows:

| | Ingredients | Gms. |
|---|---|---|
| (a) | 7α-methyl-estr-5-ene-3β,17β-diol acetate | 10 |
| (b) | Light liquid petrolatum | 250 |
| (c) | Wool fat | 200 |
| (d) | White petrolatum q.s. ad | 1000 |

The wool fat, white petrolatum and 200 gms. of the light liquid petrolatum are liquified and held at 43° C. The active ingredient is mixed with the remaining liquid petrolatum and passed through a colloid mill. After passing through the mill, the mixture is stirred into the melt, and the melt is permitted to cool with continued stirring until congealed.

EXAMPLE 11

Preparation of a Vaginal Foam

One hundred containers of an aerosol foam for vaginal use each contaning 1.0% of 7α-methyl-estr-5-ene-3β,17β-diol are prepared from the following formulation:

| | Ingredients | Gms. |
|---|---|---|
| (a) | 7α-methyl-estr-5-ene-3β,17β-diol | 30 |
| (b) | Polyoxyethylated high molecular weight fatty alcohol | 10 |
| (c) | Oleate ester of sorbitol | 30 |
| (d) | Propellant | 300 |
| (e) | Propylene glycol q.s. ad | 3000 |

The polyoxyethylated high molecular weight fatty alcohol foaming agent is dissolved in the propylene glycol vehicle. The 7α-methyl-estr-5-ene-3β,17β-diol is dispersed with the oleate ester of sorbitol surfactant with the aid of gentle heat, if necessary, and added to the propylene glycol solution. One hundred suitable aerosol containers are equally filled, capped with an aerosol valve and gassed using a propellant mixture of 4 parts of dichlorotetrafluoroethane to 1 part of dichlorodifluoromethane.

We claim:

1. A method of terminating pregnancy in higher female primates which comprises administering to said primates a therapeutic amount of a 7α-methyl-estr-5-ene-3β,17β-diol having the formula

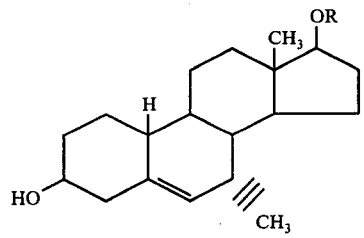

wherein R is selected from the group consisting of hydrogen and acyl having from 1 to 12 carbon atoms; administering said diol on or about 21 days following the onset of the last menstrual bleeding for a period of from 1 to 14 days or until menstrual bleeding again commences, whichever first occurs.

2. A method according to claim 1 wherein the therapeutic amount is from 0.1 mg. to 500 mg. per day.

3. A method according to claim 2 wherein the therapeutic amount is administered as a single dose.

4. A method according to claim 1 wherein the primate is human.

5. A method according to claim 2 wherein the primate is human.

6. A method of terminating the implantation of a fertilized ovum in higher female primates which comprises administering to said primates at the time of implantation a therapeutic amount of 7α-methyl-estr-5-ene-3β,17β-diol having the formula

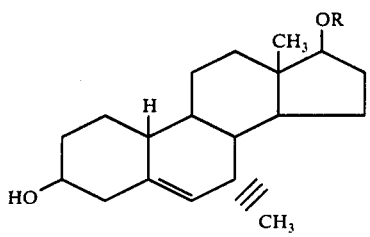

wherein R is selected from the group consisting of hydrogen and acyl having from 1 to 12 carbon atoms.

7. A method according to claim 6 wherein the therapeutic amount is from 0.1 mg. to 500 mg. per day.

8. A method according to claim 7 wherein the therapeutic amount is administered as a single dose.

9. A method according to claim 6 wherein the primate is human and administration is from day 21 to day 35 of the menstrual cycle.

* * * * *